United States Patent [19]

Di Cesare

[11] Patent Number: 5,716,784
[45] Date of Patent: Feb. 10, 1998

[54] FLUORESCENCE DETECTION ASSAY FOR HOMOGENEOUS PCR HYBRIDIZATION SYSTEMS

[75] Inventor: Joseph L. Di Cesare, Redding, Conn.

[73] Assignee: The Perkin-Elmer Corporation, Norwalk, Conn.

[21] Appl. No.: 596,560

[22] Filed: Feb. 5, 1996

[51] Int. Cl.$^6$ .............................. C12Q 1/68; C07H 21/00
[52] U.S. Cl. ........................... 435/6; 536/25.32; 435/91.2
[58] Field of Search ..................... 435/91.2, 6; 536/25.32

[56] References Cited

U.S. PATENT DOCUMENTS

| | | | |
|---|---|---|---|
| 5,210,015 | 5/1993 | Gelfand et al. | 435/6 |
| 5,278,043 | 1/1994 | Bannwarth | 536/23.1 |

FOREIGN PATENT DOCUMENTS

| | | | |
|---|---|---|---|
| 0 232 967 | 8/1987 | European Pat. Off. | C12Q 1/68 |

OTHER PUBLICATIONS

Holland et al. Detection of Specific Polymerase Chain Reaction Product by Utilizing the 5'→3' Exonuclease Activity of *Thermus aquaticus*, Proc. Natl. Acad. Sci. U.S.A., 1991, vol. 88, pp. 7276–7280.
Morrison et al. Sensitive Fluorescence-Based Thermodynamic and Kinetic Measurements of DNA Hybridization in Solution 1993, vol. 32, pp. 3095–3104.
Nucleic Acids Research, vol. 22, No. 4, 662–668 (1994).
Nucleic Acids Research, vol. 19, No. 15, 4097–4102 (1991).
Biochemistry, vol. 32, 3095–3104 (1993).
Clinical Chemistry, vol. 39, No. 9, 1939–1943 (1993).
Proc. Natl. Acad. Sci., USA, Biochemistry, vol. 86, 9717–9721 (Dec. 1989).
Proc. Natl. Acad. Sci., USA, Biochemistry, vol. 88, 7276–7280 (Aug. 1991).
L. Morrisson et al., "Analytical Biochemistry", vol. 32, 3095–3104 (1993).

*Primary Examiner*—Kenneth R. Horlick
*Assistant Examiner*—J. Tung
*Attorney, Agent, or Firm*—George W. Rauchfuss, Jr.

[57] ABSTRACT

An improved assay system for homogeneous assay detection and/or measuring target nucleic acid sequence replicated in a PCR amplification procedure is provided by employing a nucleic acid polymerase having 5' to 3' exonuclease activity and devoid of 3' to 5' exonuclease activity, oligonucleotide analytical probe blocked against chain extension at its 3' terminus and labeled at its 5' terminus with an energy transfer donor fluorophore, and oligonucleotide detection probe labeled at its 3' terminus with an energy transfer acceptor fluorophore, said probes being complements of each other but differing in nucleotide length so that their Tm's are at least 10° C. apart, the Tm of the oligonucleotide analytical probe is equal to or greater than the Tm's of the oligonucleotide primers used in the PCR amplification procedure and the Tm of the oligonucleotide detection probe is lower than the temperature required to conduct the PCR thermal cycling steps of the PCR amplification procedure so that during the PCR thermal cyclic steps 5' fluorophore labeled nucleotide fragments are produced during the PCR extension phase by the 5' to 3' exonuclease activity of the nucleic acid polymerase on oligonucleotide analytical probe annealed to denatured strands of the target nucleic acid sequence. Detection or measurement of either (a) the 5' fluorophore labeled nucleotide fragments produced during the thermal cyclic steps and measured by fluorescence polarization or (b) oligonucleotide analytical probe hybridized to oligonucleotide detection probe measured spectrophotometrically by energy transfer measurement, provide a measure of the amount of oligonucleotide analytical probe used up in the amplification of the target nucleic acid sequence and thus provide a measure of amount of target nucleic acid sequence amplified in the PCR replication procedure.

13 Claims, No Drawings

FLUORESCENCE DETECTION ASSAY FOR HOMOGENEOUS PCR HYBRIDIZATION SYSTEMS

FIELD OF THE INVENTION

This invention relates to non-radiative energy transfer probes for use in DNA or RNA polynucleotidehybridization assays to provide improved detection characteristics and more particularly to an assay system with improved sensitivity for detection of polynucleotide sequences using such non-radiative probes in PCR hybridization assays, particularly homogeneous PCR hybridization assays.

BACKGROUND OF THE INVENTION

Polymerase chain reaction (PCR) is a recently developed significant and powerful technique for polynucleotide amplification. The technique is disclosed, for example, in U.S. Pat. Nos. 4,683,195; 4,683,202; 4,800,159 and 4,965,188. PCR may be generally described as follows. The technique is an enzymatic, in vitro synthesis method for replicating or amplifying specific target polynucleotide sequences in samples. The technique employs polymerase, deoxynucleoside triphosphates and two oligonucleotide primers that hybridize to opposite strands of the polynucleotide sample and flank the region of interest in the target polynucleotide sequence. Experimental amplification of the target sequence is obtained by a repetitive series of steps comprising template denaturation, primer annealing and extension of the annealed primers by polymerase, generally referred to as thermal cycling steps. Such a PCR technique is capable of producing amplification of the target sequence by a factor of up to about $10^9$.

Once a polynucleotide sample is subject to amplification in a PCR amplification procedure, detection of the presence or absence of the desired target sequence can be accomplished by a variety of radiative (isotopic) or non-radiative (non-isotopic) hybridization detection methods. Such hybridization assays are disclosed, for example, in Methods of Enzymology, Vol. 68, pp 379–469 (1979) and Vol. 65, Part 1, pp 468–478 (1978) and in Analytical Biochemistry, 138, pp 267–284 (1984) and describe the use of radiative (isotopic) labeled and fluorescent labeled detection probes. In recent time, much effort has been made to move away from radiative labeled probes and towards the use of fluorescent-labeled probes.

Currently, assay formats are predominantly based on heterogeneous hybridization in which the target nucleic acid is sequestered on a solid support to permit separation of hybridized and unhybridized detection probes. While these heterogeneous assays display good sensitivity, the necessity for separation and wash steps makes automation difficult.

A number of homogeneous hybridization assays employ the properties of donor and acceptor fluorophore-labeled oligonucleotides to transfer or quench fluorescence energy when hybridized to the analyte. However, various problems have been encountered when using polynucleotide probes labeled with generally available fluorophores. One of the most significant problems resides in limited sensitivity for direct detection of the labeled probe in the assay system. For most hybridization assays, a sensitivity or detection level of at least 10' mole of labeled probe ($10^6$ target molecule) is desirable. While many fluorophores inherently have this level of sensitivity, secondary interference from the sample and components of the assay system prevent these levels of detection from being reached. At a level of $10^{-18}$ mole of fluorescent probe, fluorescence from the sample itself, Rayleigh scatter, reflection from support materials and Raman (water) scatter can produce background signals many orders of magnitude higher than the signal from the fluorescent probe.

While simpler to carry out homogeneous assay procedures based on chemi- or bio- luminescent probes have been reported which do not involve radiative energy transfer, such as in Clin. Chem., 29(9), pp 1604–1608 (1983), unbound labeled probe remains in solution causing undesirable interfering background signal.

It is therefore desirable to provide an improved assay procedure for enhanced detection of target polynucleotide samples using non-radiative energy transfer permitting both PCR amplification of the target and release of a label for detection to be accomplished in a reaction system without requiring a multitude of handling or separation steps of the amplified product and especially useful for homogeneous assays in which an assay signal can be generated while the target sequence is amplified and without requiring separation steps.

SUMMARY OF THE INVENTION

An improved assay system for homogeneous assay detection and/or measuring target nucleic acid sequence replicated in a PCR amplification procedure is provided by employing a nucleic acid polymerase having 5' to 3' exonuclease activity and devoid of 3' to 5' exonuclease activity, oligonucleotide analytical probe blocked against chain extension at its 3' terminus and labeled at its 5' terminus with an energy transfer donor fluorophore, and oligonucleotide detection probe labeled at its 3' terminus with an energy transfer acceptor fluorophore, said probes being complements of each other but differing in nucleotide length so that their Tm's are at least 10° C. apart, preferably at least 15° or 20° C. apart, and the Tm of the oligonucleotide analytical probe is equal to or greater, preferably at least several degrees higher, than the Tm's of the oligonucleotide primers used in the PCR amplification procedure and the Tm of the oligonucleotide detection probe is lower than the temperature required to conduct the PCR thermal cycling steps of the PCR amplification procedure so that during the PCR thermal cyclic steps 5' fluorophore labeled nucleotide fragments, generally fluorophore labeled mono- or di-nucleotide fragments, are produced during the PCR extension phase by the 5' to 3' exonuclease activity of the nucleic acid polymerase on oligonucleotide analytical probe annealed to denatured strands of the target nucleic acid sequence. Detection or measurement of either (a) the 5' fluorophore labeled nucleotide fragments produced during the thermal cyclic steps and measured by fluorescence polarization or (b) oligonucleotide analytical probe hybridized to oligonucleotide detection probe measured spectrophotometrically by energy transfer measurement, provide a measure of the amount of oligonucleotide analytical probe used up in the amplification of the target nucleic acid sequence and thus provide a measure of amount of target nucleic acid sequence amplified in the PCR replication procedure.

DETAILED DESCRIPTION OF THE INVENTION

The invention provides a process for replication and homogeneous assay detection of a target nucleic acid sequence in a sample, said process comprising:

a) providing in a PCR reaction mixture a sample suspected to contain a target nucleic acid sequence, oligonucleotide PCR primers that hybridize to opposite strands of the target nucleic acid sequence and flank the target sequence for PCR amplification of said target sequence, each of four deoxynucleoside triphosphates, nucleic acid polymerase having 5' to 3' exonuclease activity and devoid of 3' to 5' exonuclease activity, oligonucleotide analytical probe blocked against chain extension at its 3' terminus and labeled at its 5' terminus with an energy transfer donor fluorophore, oligonucleotide detection probe labeled at its 3' terminus with an energy transfer acceptor fluorophore, said oligonucleotide analytical probe and oligonucleotide detection probe are complements but differ in nucleotide length so that their Tm's are at least 10° C. apart and with the proviso that the Tm of the oligonucleotide analytical probe is equal to or greater than the Tm's of the oligonucleotide PCR primers and the Tm of the oligonucleotide detection probe is lower than the temperature at which PCR thermal cycling occurs;

b) amplifying target nucleic acid sequence in the sample under suitable PCR reaction mixture temperature conditions by a repetitive series of PCR thermal cycling steps comprising:

1) denaturing the target nucleic acid sequence into opposite strands;

2) hybridizing the oligonucleotide analytical probe within the target nucleic acid sequence of the denatured strands and hybridizing the oligonucleotide PCR primers to the denatured strands, and 3) extending the hybridized primers with the four deoxynucleoside triphosphates and the nucleic acid polymerase, and producing 5' fluorophore labeled nucleotide fragments during this extension phase by the 5' to 3' exonuclease activity of the nucleic acid polymerase on oligonucleotide analytical probe annealed to the denatured strands;

c) following amplification of the target nucleic acid sequence by one or more series of thermal cycling step spectrophotometrically detecting or measuring the amount of one or more of the following as a measure of the amount of oligonucleotide analytical probe used up in the amplification of the target nucleic acid sequence:

(1) fluorescence polarization measurement of 5' fluorophore labeled nucleotide fragments formed, and (2) fluorescence energy transfer measurement of oligonucleotide analytical probe hybridized to oligonucleotide detection probe following a further step of lowering the PCR reaction mixture temperature to a temperature below the temperature at which the thermal cycling steps occur and to a temperature at which hybridization of oligonucleotide analytical probe to the oligonucleotide detection probe occurs.

In the temperature range at which the PCR thermal cycling steps occur the oligonucleotide analytical probe anneals to a denatured strand of the target nucleic acid sequence and during the PCR extension phase the invention utilizes the 5' to 3' exonuclease activity of the nucleic acid polymerase to produce 5' fluorophore labeled nucleotide fragments by hydrolysis of the nucleotides of oligonucleotide analytical probe annealed to the denatured strand.

This invention enables a homogeneous assay to be conducted in which it is unnecessary to separate free oligonucleotide analytical probe from the hydrolyzed fluorophor labeled nucleotide fragments formed during PCR amplification due to fluorescence excitation energy transfer between the analytical, oligonucleotide probe and the oligonucleotide detection probe. Fluorescence energy transfer between a donor molecule and an acceptor molecule can be highly efficient if the molecules are in close proximity, e.g. within about 50 Å. When the molecules are within 0–10 Å, energy transfer approaching up to about 100% can be theoretically achieved if all requirements are satisfied.

In this invention a substantial amount of the oligonucleotide analytical probe muet hybridize to the oligonucleotide detection probe and efficient fluorescence energy transfer must occur between the donor fluorophore on the 5' end of the oligonucleotide analytical probe and the acceptor fluorophore on the 3' end of the oligonucleotide detection probe. In order for this to occur and not interfere with the PCR amplification process, the two probes are complements but differ in length so that their Tm's are about 10° to 20° C. apart. Thus, when a measurement is required, the PCR reaction mixture temperature is lowered to the Tm of the oligonucleotide detection probe so that annealing of the two probes occurs and energy transfer between the energy transfer donor fluorophore and the energy transfer acceptor fluorophore can result.

During each cycle of the PCR thermal cycling steps, a portion of the oligonucleotide analytical probe is hybridized to the target nucleic acid sequence. Since this probe is blocked at its 3' end, it cannot act as a primer and be extended. During each PCR thermal cycle, the oligonucleotide analytical probe is effectively removed from the path of the nucleic acid polymerase by being hydrolyzed by the polymerase into small nucleotide fragments of 1–2 nucleotide bases in length until the probe is completely removed and primer extension can continue. Among the small nucleotide fragments produced is 5' fluorophore labeled nucleotide fragments. These 5' fluorophore labeled nucleotide fragments have a very low Tm, in the order of 30° C. or below, compared to the Tm's of the oligonucleotide analytical probe and thus will not hybridize to the oligonucleotide detection probe at the detection temperature, e.g. 50° C. Therefore, the 5' fluorophore labeled fragments cannot participate in an energy transfer reaction as car the free (unhybridized) oligonucleotide analytical probe. Thus, a measurement of the fluorescence of the acceptor fluorophore is a direct measure of the extent of PCR amplification of the target nucleic acid sequence. Additionally, these small 5' fluorophore labeled nucleotide fragments can be measured relative to the amount of 5' fluorophore labeled oligonucleotide analytical probe by fluorescence polarization.

"Sample", as used herein, refers to any substance containing or presumed to contain the target nucleic acid sequence and includes a sample of tissue or fluid isolated from an individual, including but not limited to, skin, plasma, serum, spinal fluid, lymph fluid, synovial fluid, urine, tears, blood cells, organs, tumors, in vitro cell cultures constituents, for example.

The terms "energy transfer donor fluorophore" and "energy transfer acceptor fluorophore", as used herein, refer to fluorescence label pairs that act as donors and acceptor fluorophore, respectively, providing for efficient fluorescence energy transfer from the donor fluorophore to the acceptor fluorophore when the fluorophores are within close proximity, e.g. with about 50 Å. Any suitable donor and acceptor fluorophores can be employed in this invention.

Selection of the donor and acceptor fluorophores is of importance to obtain the advantages of this invention. In general, the fluorescent moiety should comprise respectively donor and acceptor moieties selected so that the emission spectrum of the donor moiety overlaps the excitation spectrum of the acceptor moiety to produce efficient non-radiative energy transfer therebetween. Wavelength maximum of the emission spectrum of the acceptor moiety should be at least about 100 nm greater than the wavelength maximum of the excitation spectrum of the donor moiety.

In addition, the fluorescent donor and acceptor pairs are preferably chosen for (1) high efficiency Forster energy transfer, (2) a large final Stoke shift (>100 nm), (3) shift of the emission as far as possible into the red portion of the visible spectrum (>600 nm), and (4) shift of the emission to a higher wavelength than the Raman water fluorescent emission produced by excitation at the donor excitation wavelength. For example, a donor fluorophore may be chosen which has its excitation maximum near a laser line (in particular Helium-Cadmium 442 nm or Argon 488 nm), a high extinction coefficient, a high quantum yield, and a good overlap of its fluorescent emission with the excitation spectrum of the acceptor fluorophore. In general, an acceptor fluorophore is preferably chosen which has a high extinction coefficient, a high quantum yield, a good overlap of its excitation with the emission of the donor, and emission in the red part of the visible spectrum (>600 nm).

As examples of suitable energy transfer donor fluorophores there may be mentioned fluorescein, Lucifer Yellow, Lucifer Yellow VS 4-acetamido-4'-isothiocyanatostilbine-2, 2-disulfonic acid, 7-diethylamine-3-(4'-isothiocyanatostilbine)-4-methylcoumarin, B-phycoerythrin, 9-acridineisocyanate derivatives, and succinimdyl-1-pyrenebutyrate. Especially preferred is fluorescein ($E_x$ 470 nm, $E_m$=520 nm).

As examples of suitable energy transfer acceptor fluorophores there may be mentioned Texas Red, Lissamine rhodamine B-sulfonyl chloride, tetramethyl rhodamine isothiocyanate, rhodamine x isothiocyanate, erythrosin isothiocyanate and diethylenetriamine pentaacetate chelates with lanthanide ions. Especially preferred is rhodamine ($E_x$ 540 nm, $E_m$=600 nm).

Any suitable nucleic acid polymerase having 5' to 3' exonuclease activity and devoid of 3' to 5' exonuclease activity can be employed in the procedure of this invention. The nucleic acid polymerase hydrolyses the oligonucleotide analytical probe only when the probe is hybridized to the target nucleic acid sequence. Preferably employed is a thermostable nucleic acid DNA polymerase, such as those disclosed in U.S. Pat. No. 4,889,818. Especially preferred for use is the *Thermus aquaticus* DNA polymerase available from Perkin-Elmer as AmpliTaq® DNA polymerase.

The oligonucleotide primers and probes can be synthesized in a variety of known ways, such as on any Perkin-Elmer Applied Biosystem DNA synthesizer. The oligonucleotide analytical probe is synthesized with 3' phosphate to prevent extension. Chemical methods for incorporating fluorophore labels into 5' terminus of the polynucleotide probes are disclosed for example in PCT Application WO 84/03285 dated Aug. 30, 1985. Oligonucleotide probes can be synthesized with a 3' phosphate moiety and can be 5' end-labeled using a 3'-phosphatase-free polynucleotide kinase.

The invention is exemplified by the following illustrative, but not limiting, example of an improved assay procedure for PCR amplification of the 134 base pair (location 1126–1259) gag region of HIV-2 genome.

The primers used for the PCR amplification are Gene-Amplimer® HIV primers SK 145 (modified by removing 5 bases at the 5' end) and SK 431, available from Perkin-Elmer, and whose nucleotides sequences, respectively, are as follows:

SEQ. ID No.: 1 5'-GGGGACATCAAGCAGCCATGCA AAT-3' 1126–1150 (HIV-2)

SEQ. ID No.: 2 5'- TGCTATGTCAGTTCCCCTTGGT TCTCT-3' 1233–1259 (HIV-2)

and whose Tm's, respectively, are 66.2° C. and 66.1° C.

The oligonucleotide analytical probe is GeneAmplimer® HIV probe SK 102(+), available from Perkin-Elmer, modified by blocking its 3' end with phosphate so that it cannot act as a primer and cannot be extended and by labeling its 5' end with fluorescein as an energy transfer donor. The nucleotide sequence of said SK 102(+) probe, whose Tm is 69.8° C., is as follows:

SEQ. ID No.: 3 5'- XGAGACCATCAATGAGGAAGC TGCAGAATGGGAT$_p$-3' 1158–1190 (HIV-2)

wherein X is the fluorophore label fluorescein and p indicates that the 3' terminus is blocked with a phosphate moiety.

The oligonucleotide detection probe is a complement to probe SK 102(+), labeled at its 3' end with rhodamine as an energy transfer acceptor. The nucleotide sequence of said probe, whose Tm is 54.8° C., is as follows:

SEQ. ID No.: 4 3'-ZCTCTGGTAGTTACTCCT-5' wherein Z is the fluorophore label rhodamine.

The nucleic acid polymerase used in AmpliTaq® DNA polymerase (Perkin-Elmer).

PCR amplification of the 134 bp target DNA fragment sequence of the gag region of the HIV-2 genome is accomplished by providing a 100 µl PCR reaction mixture of the target nucleic acid sequence, 1.25 units *Thermus aquaticus* DNA polymerase, 500 nM each of the two PCR primers, modified SK 145 and SK 431, and 500 nM of each of the analytical and detection probes in water and a suitable PCR buffer system.

The PCR reaction mixture is subjected to the PCR thermal cyclic steps of denaturation at about 95° C. and annealing/extending at about 65° C. in a Perkin-Elmer thermal cycler in the usual manner. During the PCR thermal cycling steps 5'-fluorophore labeled nucleotide fragments are produced and this product accumulates as a function of the amount of amplification. After about 20 thermal cycles, the temperature is dropped to about 50° C. and after about 10 seconds, the amount of fluorescence associated with oligonucleotide analytical probe SK 102(+) hybridized to oligonucleotide detection probe in the thermally cycled PCR reaction mixture is measured spectrophotometrically using a Perkin-Elmer model LS-50B or similar fluorometer or fiber optic fluorometer set at 50° C. by subjecting an aliquot of the thermally cycled 50° C. PCR reaction mixture to an excitation wavelength of 470 nm and measuring the hybridized rhodamine fluorophore emission wavelength at 600 nm. The measurement of fluorescence of the rhodamine labeled detection probe hybridized to the fluorescein labeled analytical probe is a measure of the amount of oligonucleotide analytical probe SK 102(+) used up in the amplification/replication of the target gag nucleotide sequence and this is also a measure of the degree of amplification/replication of the target gag nucleotide sequence.

Alternatively, the thermally cycled PCR reaction mixture can be subjected to fluorescence polarization measurement to measure the degree of polarization, i.e. the ratio of 5'-fluorescein labeled nucleotide fragments to fluorescein labeled analytical probe SK 102(+).

When fluorescent molecules are excited with plane polarized light, they emit light in the same polarized plane, provided the molecule remains stationary throughout the excited state, which in the case of fluorescein is 4 nsec. However, if the excited molecule rotates or tumbles during the excited state, then light is emitted in a plane different from the excitation plane. If fluorescently labeled molecules are large, they move little during the excited state interval, and the emitted light remains highly polarized with respect to the excitation plane. However, if fluorescently labeled molecules are small, they rotate or tumble faster and the resulting emitted light is depolarized relative to the excitation plane. Therefore, fluorescence polarization can be used to follow biochemical reactions that result in a change of size of a fluorescently labeled molecule.

In the PCR amplification process according to this invention, there is such a change in a fluorescently labeled molecule, i.e. 5' fluorophore labeled oligonucleotide analytical probe annealed to the denatured strands is hydrolyzed by the 5' to 3' exonuclease activity of the nucleic acid polymerase forming the 5' fluorophore labeled nucleotide fragments. The 5' fluorophore labeled oligonucleotide analytical probe is the large fluorescently labeled molecule that moves only very little, whereas the 5' fluorophore labeled nucleotide fragments are the small molecules that rotate or tumble during the excited state interval.

Employing fluorescent polarization as a measure of the extent of the PCR amplification process is especially beneficial since (1) measurements can be performed in a single-phase reaction mixture, (2) measurements can be taken in real time, and (3) no manipulations, separations or transfers of the PCR reaction mixture are necessary.

Fluorescence polarization measurement (p) is defined as $$p = \frac{Fv - Fh}{Fv - Fh}$$

where Fv is the intensity of the emission light parallel to the excitation light plane and Fh is the intensity of the emission light perpendicular to the excitation light plane and p is a dimensionless number and is usually expressed in terms of mP (millipolarization units). Thus, a fluorescence polarization measurement of the PCR reaction mixture would be a measure of the ratio of 5' fluorophore labeled nucleotide fragments to the 5' fluorophore labeled nucleotide fragments to the 5' fluorophore labeled oligonucleotide analytical probe. As the PCR amplification reaction proceeds, polarization at the specific excitation and emission wavelengths employed would decrease as more 5' fluorophore labeled nucleotide fragments are generated by the 5' to 3' exonuclease activity of the nucleic acid polymerase.

Using the LS-50B or similar fluorometer or fiber optic fluorometer set at 50° C. with an excitation wavelength of 470 nm and an emission wavelength of 520 nm, two emission light intensity measurements are taken, one with the polarizing filter of the instrument in parallel and a second with the polarizing filter perpendicular to the plane of the polarized light. The ratio of the two measurements is an indication of the degree of polarization of the molecule, i.e. the ratio 5'-fluorescein labeled nucleotide fragments to the fluorescein labeled oligonucleotide analytical probe SK 102 (+).

Using either of the two aforedescribed fluorescence measurements provides data relating to oligonucleotide analytical probe SK 102(+) used up in the amplification/replication and from this data one can calculate back to determine how much target nucleic acid sequence was present in the sample employed.

The improved homogeneous assay procedure of this invention provides high levels of specificity, sensitivity and reproducibility and can be conducted concurrently with target nucleic acid amplification.

With the foregoing description of the invention, those skilled in the art will appreciate that modifications may be made to the invention without departing from the spirit thereof. Therefore, it is not intended that the scope of the invention be limited to the specific embodiments illustrated and described.

---

I claim:

1. A process for replication and homogeneous assay detection of a target nucleic acid sequence in a sample, said process comprising:

a) providing in a PCR reaction mixture a sample suspected to contain a target nucleic acid sequence, oligonucleotide PCR primers that hybridize to opposite strands of the target nucleic acid sequence and flank the target sequence for PCR amplification of said target sequence, each of four deoxynucleoside triphosphates, nucleic acid polymerase having 5' to 3' exonuclease activity and devoid of 3' to 5' exonuclease activity, oligonucleotide analytical probe blocked against chain extension at its 3' terminus and labeled at its 5' terminus with energy transfer donor fluorophore, and oligonucleotide detection probe labeled at its 3' terminus with energy transfer acceptor fluorophore, said oligonucleotide analytical probe and oligonucleotide detection probe are complements but differ in nucleotide length so that their Tm's are at least 10° C. apart and with the proviso that the Tm of the oligonucleotide analytical probe is equal to or greater than the Tm's of the oligonucleotide PCR primers and the Tm of the oligonucleotide detection probe is lower than the temperature at which PCR thermal cycling occurs;

b) amplifying target nucleic acid sequence in the sample under suitable PCR reaction mixture temperature conditions by a repetitive series of PCR thermal cycling steps comprising:

1) denaturing the target nucleic acid sequence into opposite strands;

2) hybridizing the oligonucleotide PCR primers and the oligonucleotide analytical probe to the denatured strands, and 3) extending the hybridized primers with the four deoxynucleoside triphosphates and the nucleic acid polymerase, and producing 5' fluorophore labeled nucleotide fragments during this extension phase by the 5' to 3' exonuclease activity of the nucleic acid polymerase on oligonucleotide analytical probe annealed to the denatured strands;

c) following amplification of the target nucleic acid sequence by one or more series of said thermal cycling steps, spectrophotometrically detecting or measuring the amount of one or more of the following as a measure of the amount of oligonucleotide analytical probe used up in the amplification of the target nucleic acid sequence:

(1) fluorescence polarization measurement of 5' fluorophore labeled nucleotide fragments formed, and (2) fluorescence energy transfer measurement of oligonucleotide analytical probe hybridized to oligonucleotide detection probe following a further step of lowering the PCR reaction mixture temperature to a temperature below the temperature at which the thermal cycling steps occur and to a temperature at which hybridization of the oligonucleotide analytical probe to the oligonucleotide detection probe occurs.

2. The process for replication and detection of a target nucleic acid sequence according to claim 1 wherein 5' fluorophore labeled nucleotide fragments formed are detected or measured.

3. The process for replication and detection of a target nucleic acid sequence according to claim 2 wherein oligonucleotide analytical probe hybridized to oligonucleotide detection probe is detected or measured.

4. The process for replication and detection of a target nucleic acid sequence according to claim 3 wherein the Tm's of said oligonucleotide analytical probe and said oligonucleotide detection probe are at least 15° C. apart and the Tm of the oligonucleotide detection probe is 55° C. or less.

5. The process for replication and detection of a target nucleic acid sequence according to claim 3 wherein the PCR thermal cycling steps occur at a temperature within the range of about 65° C. to about 95° C. and hybridization of the oligonucleotide analytical probe to the oligonucleotide detection probe occurs at a temperature of about 55° C. or below.

6. The process for replication and detection of a target nucleic acid sequence according to claim 1 wherein the nucleic acid polymerase is *Thermus aquaticus* DNA polymerase.

7. The process for replication and detection of a target nucleic acid sequence according to claim 5 wherein the nucleic acid polymerase is *Thermus aquaticus* DNA polymerase.

8. The process for replication and detection of a target nucleic acid sequence according to claim 1 wherein the oligonucleotide analytical probe is labeled with a fluorescein moiety as an energy transfer donor fluorophore and the oligonucleotide detection probe is labeled with a rhodamine moiety as the energy transfer acceptor fluorophore.

9. The process for replication and detection of a target nucleic acid sequence according to claim 5 wherein the oligonucleotide analytical probe is labeled with a fluorescein moiety as an energy transfer donor fluorophore and the oligonucleotide detection probe is labeled with a rhodamine moiety as the energy transfer acceptor fluorophore.

10. The process for replication and detection of a target nucleic acid sequence according to claim 8 comprising detecting or measuring the fluorophore nucleotide fragments spectroscopically at an excitation wavelength of about 470 nm and at an emission wavelength of about 520 nm.

11. The process for replication and detection of a target nucleic acid sequence according to claim 9 comprising detecting or measuring oligonucleotide analytical probe hybridized to oligonucleotide detection probe spectroscopically at an excitation wavelength of about 470 nm and at an emission wavelength of about 600 nm.

12. The process for replication and detection of a target nucleic acid sequence according to claim 1 wherein the energy transfer donor fluorophore is a moiety selected from the group consisting of fluorescein, Lucifer Yellow, Lucifer Yellow VS 4-acetamido-4-isothiocyanatostilbine-2,2-disulfonic acid, 7-diethylamine-3-(4-isothiocyanatostilbine)-4-methylcoumarin, B-phycoerythrin, 9-acridineisocyanate derivatives, and succinimdyl-1-pyrenebutyrate, and the energy transfer acceptor fluorophore is a moiety selected from the group consisting of Texas Red, Lissamine rhodamine B-sulfonyl chloride, tetramethyl rhodamine isothiocyanate, rhodamine x isothiocyanate, erythrosin isothiocyanate and diethylenetriamine pentaacetate chelates with lanthanide ions.

13. The process for replication and detection of a target nucleic acid sequence according to claim 3 wherein the energy transfer donor fluorophore is a moiety selected from the group consisting of fluorescein, Lucifer Yellow, Lucifer Yellow VS 4-acetamido-4'-isothiocyanatostilbine-2,2-disulfonic acid, 7-diethylamine-3-(4'-isothiocyanatostilbine)-4-methylcoumarin, B-phycoerythrin, 9-acridineisocyanate derivatives, and succinimdyl-1-pyrenebutyrate, and the energy transfer acceptor fluorophore is a moiety selected from the group consisting of Texas Red, Lissamine rhodamine B-sulfonyl chloride, tetramethyl rhodamine isothiocyanate, rhodamine x isothiocyanate, erythrosin isothiocyanate and diethylenetriamine pentaacetate chelates with lanthanide ions.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 1:

GGGGACATCA AGCAGCCATG CAAAT 25

( 2 ) INFORMATION FOR SEQ ID NO: 2:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 2:

TGCTATGTCA GTTCCCCTTG GTTCTCT 27

(  2  ) INFORMATION FOR SEQ ID NO: 3:

(  i  ) SEQUENCE CHARACTERISTICS:
( A ) LENGTH: 33 bases
( B ) TYPE: nucleic acid
( C ) STRANDEDNESS: single
( D ) TOPOLOGY: linear (  i i  ) MOLECULE TYPE: Other nucleic acid (  x i  ) SEQUENCE DESCRIPTION: SEQ ID NO: 3:

GAGACCATCA ATGAGGAAGC TGCAGAATGG GAT    33

(  2  ) INFORMATION FOR SEQ ID NO: 4:

(  i  ) SEQUENCE CHARACTERISTICS:
( A ) LENGTH: 17 bases
( B ) TYPE: nucleic acid
( C ) STRANDEDNESS: single
( D ) TOPOLOGY: linear (  i i  ) MOLECULE TYPE: Other nucleic acid (  x i  ) SEQUENCE DESCRIPTION: SEQ ID NO: 4:

CTCTGGTAGT TACTCCT    17